United States Patent [19]

Krämer et al.

[11] 4,371,708
[45] Feb. 1, 1983

[54] 4-SUBSTITUTED 3,3-DIMETHYL-BUTAN-2-ONES, PROCESSES FOR THEIR PREPARATION AND THEIR USE AS INTERMEDIATE PRODUCTS

[75] Inventors: Wolfgang Krämer; Hans-Ludwig Elbe, both of Wuppertal, Fed. Rep. of Germany

[73] Assignee: Bayer Aktiengesellschaft, Leverkusen, Fed. Rep. of Germany

[21] Appl. No.: 265,269

[22] Filed: May 20, 1981

[30] Foreign Application Priority Data

Jun. 7, 1980 [DE] Fed. Rep. of Germany ....... 3021516

[51] Int. Cl.³ ........................................... C07C 151/00
[52] U.S. Cl. ....................................... 568/31; 568/32; 568/33; 568/42; 568/337; 568/414; 568/416
[58] Field of Search .............. 568/31, 350, 414, 419, 568/42, 43, 303, 305, 306, 307, 308, 414, 416, 419, 382, 32, 33, 337

[56] References Cited

U.S. PATENT DOCUMENTS

| 2,374,283 | 4/1945 | Grün et al. | 568/414 |
| 3,625,836 | 12/1971 | Stansbury | 568/414 |
| 4,141,919 | 2/1979 | Gremmelmaier | 568/414 |
| 4,254,132 | 3/1981 | Kramer | 568/414 |
| 4,255,434 | 3/1981 | Kramer | 568/414 |
| 4,267,381 | 5/1981 | Jautelat et al. | 568/419 |

FOREIGN PATENT DOCUMENTS

| 253931 | 3/1964 | Australia | 568/31 |
| 22321 | 1/1981 | European Pat. Off. | 568/336 |
| 38-4861 | 4/1963 | Japan | 568/414 |
| 820095 | 9/1959 | United Kingdom | 568/414 |
| 986714 | 3/1965 | United Kingdom | 568/414 |

OTHER PUBLICATIONS

Bisagni et al., "Chemical Abstract", vol. 72 (1970), p12289a.
Hayami "Tetrahedron Letters No. 11, pp. 1385–1386, Pergaman Press Britain.

*Primary Examiner*—Werren B. Lone
*Attorney, Agent, or Firm*—Sprung, Horn, Kramer & Woods

[57] ABSTRACT

4-substituted 3,3-dimethyl-butan-2-ones of the formula

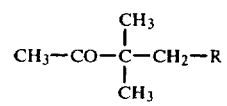

in which
R represents cyano or the grouping —X—R¹,
wherein
R¹ represents n-alkyl with 1 to 4 carbon atoms, isopropyl, isobutyl, sec.-butyl, alkenyl with 3 to 4 carbon atoms, alkynyl with 3 to 4 carbon atoms, optionally substituted aryl or substituted aralkyl, or represents cyano provided that X represents —O— or —S—, and
X represents —O—, —S—, —SO—, or —SO₂—,
which are intermediates for the synthesis of fungicides.

7 Claims, No Drawings

4-SUBSTITUTED 3,3-DIMETHYL-BUTAN-2-ONES, PROCESSES FOR THEIR PREPARATION AND THEIR USE AS INTERMEDIATE PRODUCTS

The present invention relates to certain new 4-substituted 3,3-dimethyl-butan-2-ones, which can be used as intermediate products for the synthesis of plant protection agents, and to a process for their preparation.

The present invention provides, as new compounds, the 4-substituted, 3,3-dimethyl-butan-2-ones of the general formula

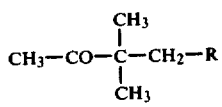 (I)

in which
R represents cyano or the grouping $—X—R^1$ wherein
$R^1$ represents n-alkyl with 1 to 4 carbon atoms, isopropyl, isobutyl, sec.-butyl; alkenyl with 3 to 4 carbon atoms, alkynyl with 3 to 4 carbon atoms, optionally substituted aryl or substituted aralkyl, or represents cyano provided that
X represents —O— or —S—, and
X represents —O—, —S—, —SO— or —SO$_2$—.

Preferably, in this formula,
R represents the grouping $—X—R^1$ or cyano, and
$R^1$ represents n-alkyl with 1 to 4 carbon atoms, isopropyl, isobutyl or sec.-butyl; alkenyl or alkynyl with in either case 3 to 4 carbon atoms; optionally substituted aryl with 6 to 10 carbon atoms or substituted aralkyl with 6 to 10 carbon atoms in the aryl part and 1 to 2 carbon atoms in the alkyl part, the or each substituent on the aryl in either case being preferably selected from halogen, cyano, nitro, alkoxy-carbonyl with 1 to 4 carbon atoms in the alkyl part, alkyl and alkoxy with in either case 1 to 4 carbon atoms, dialkylamino with 1 to 2 carbon atoms in each alkyl part and phenyl which is itself optionally substituted by halogen; or cyano, provided that X represents oxygen or sulphur.

X preferably has the meaning given in the definition of the invention.

Particularly preferred compounds of the formula (I) are those in which R and X have the meanings given in the definition of the invention and $R^1$ represents methyl, ethyl, n-propyl, isopropyl, n-butyl, isobutyl, sec.-butyl, allyl, propargyl or optionally substituted phenyl or substituted benzyl, the substituents being selected from fluorine, chlorine, bromine, cyano, nitro, methoxycarbonyl, methyl, ethyl, isopropyl, tert.-butyl, methoxy, dimethylamino and phenyl which is optionally substituted by fluorine and/or chlorine; or $R^1$ represents cyano, provided that X represents oxygen or sulphur.

The invention also provides a process for the preparation of a 4-substituted 3,3-dimethyl-butan-2-one of the formula (I) in which (a) a butan-2-one derivative of the general formula

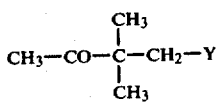 (II)

in which

Y represents chlorine, bromine or the grouping $—O—SO_2—R^2$, wherein
$R^2$ represents alkyl or optionally substituted aryl, is reacted with a compound of the general formula $$R^3—M \quad (III),$$

in which
$R^3$ represents the grouping $—X^1—R^4$ or cyano,
$R^4$ represents n-alkyl with 1 to 4 carbon atoms, isopropyl, isobutyl, sec.-butyl, alkenyl or alkynyl with in either case 3 to 4 carbon atoms, optionally substituted aryl, substituted aralkyl or cyano,
$X^1$ represents oxygen or sulphur and
M represents an alkali metal or hydrogen, in the presence of a diluent and if appropriate in the presence of an acid-binding agent, or (b) 3,3-dimethyl-4-hydroxy-butan-2-one, of the formula

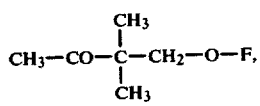 (IV)

is reacted with a compound of the general formula $$Y'—R^5 \quad (V),$$

in which
$R^5$ represents n-alkyl with 1 to 4 carbon atoms; isopropyl, isobutyl, sec.-butyl, alkenyl or alkynyl with in either case 3 to 4 carbon atoms or substituted aralkyl,
Y' represents chlorine, bromine or the grouping $—O—SO_2—R^6$ and
$R^6$ represents alkyl, alkoxy or optionally substituted aryl, if appropriate in the presence of a diluent and if appropriate in the presence of an acid-binding agent, or (c) a compound of the general formula

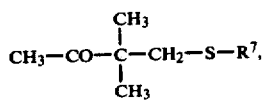 (Ia)

in which
$R^7$ represents n-alkyl with 1 to 4 carbon atoms, isopropyl, isobutyl, sec.-butyl, alkenyl or alkynyl with in each case 3 to 4 carbon atoms, optionally substituted aryl or substituted aralkyl, obtainable by process variant (a), is reacted with an oxidizing agent in the customary manner.

If, for example, 3,3-dimethyl-4-tosyloxy-butan-2-one and the sodium salt of 4-chlorophenol are used as starting substances in the process variant (a), the course of the reaction can be represented by the following equation:

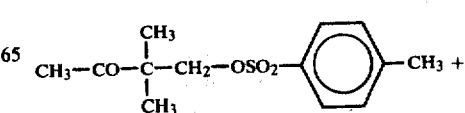

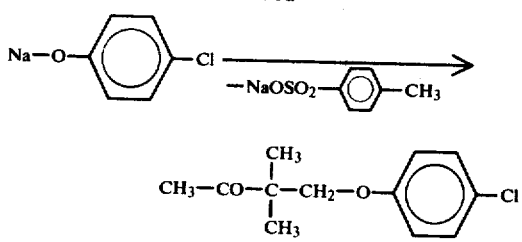

If, for example, 4-chloropinacolin and thiophenol are used as starting substances in process variant (a), the course of the reaction can be represented by the following equation:

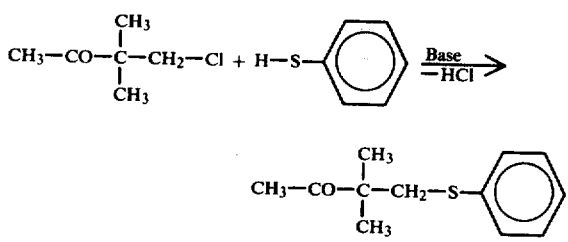

If, for example, 4-hydroxypinacolin and dimethyl sulphate are used as starting substances in process variant (b), the course of the reaction can be represented by the following equation:

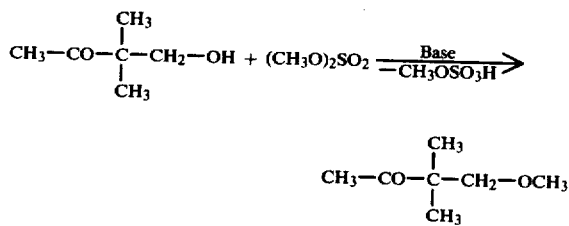

If, for example, 3,3-dimethyl-4-phenylmercaptobutan-2-one is used as the starting substance in process variant (c) and hydrogen peroxide/glacial acetic acid is used as the oxidizing agent, the course of the reaction can be represented by the following equation:

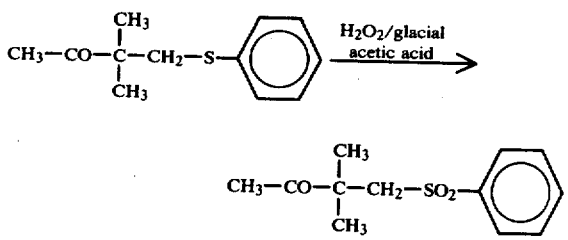

The formula (II) provides a general definition of the butan-2-one derivatives to be used as starting substances for process variant (a). In this formula, Y preferably represents chlorine, bromine or the grouping —O—SO$_2$—R$^2$, R$^2$ preferably representing alkyl with 1 to 4 carbon atoms or optionally substituted aryl with 6 to 10 carbon atoms (especially phenyl), a preferred substituent being alkyl with 1 to 4 carbon atoms.

The butan-2-one derivatives of the formula (II) are known (see, for example, DE-OS (German Published Specification) No. 2,632,603 [Le A 17 273] and J. Org. Chem. 35, 2391 (1970)), or they can be obtained in a generally known manner from 3,3-dimethyl-4-hydroxybutan-2-one (see also the preparative examples herein).

The formula (III) provides a general definition of the compounds also to be used as starting substances for process variant (a). In this formula, R$^3$ preferably represents the grouping —X$^1$—R$^4$ or cyano. X$^1$ preferably represents oxygen or sulphur. R$^4$ preferably represents n-alkyl with 1 to 4 carbon atoms, isopropyl, isobutyl or sec.-butyl; alkenyl or alkynyl with in either case 3 to 4 carbon atoms; cyano; or optionally substituted phenyl or substituted benzyl, possible substituents being halogen, cyano, nitro, alkoxycarbonyl with 1 to 4 carbon atoms in the alkyl part, alkyl and alkoxy with in each case 1 to 4 carbon atoms, dialkylamino with 1 to 2 carbon atoms in each alkyl part, and phenyl which is optionally substituted by halogen. M preferably represents potassium, sodium or hydrogen.

The compounds of the formula (III) are generally known compounds of organic chemistry. If appropriate, they are employed as products prepared in situ.

3,3-Dimethyl-4-hydroxy-butan-2-one of the formula (IV), which is to be used as a starting substance for process variant (b), is known (see, for example, DE-OS (German Published Specification) No. 2,632,603).

The formula (V) provides a general definition of the compounds also to be used as starting substances for process variant (b). In this formula, R$^5$ preferably represents n-alkyl with 1 to 4 carbon atoms, isopropyl, isobutyl or sec.-butyl; alkenyl or alkynyl with in either case 3 to 4 carbon atoms; or optionally substituted benzyl, preferred substituents being the substituents which have already been mentioned above.

Y' preferably represents chlorine, bromine or the grouping —O—SO$_2$—R$^6$, R$^6$ preferably representing alkyl or alkoxy with in either case 1 to 4 carbon atoms or phenyl which is optionally substituted by alkyl with 1 to 4 carbon atoms.

The compounds of the formula (V) are generally known compounds of organic chemistry.

The compounds of the formula (Ia), to be used as starting substances for process variant (c), are themselves compounds according to the invention.

Preferred diluents for the process variant (a) are organic solvents. These include, as preferences, ethers, such as diethyl ether and dioxane; alcohols, such as glycol; aliphatic and aromatic hydrocarbons, such as ligroin, petroleum ether, benzene, toluene or xylene; and formamides, such as dimethylformamide.

If appropriate, process variant (a) is carried out in the presence of an acid-binding agent. It is possible to add any of the inorganic or organic acid-binding agents which can customarily be used, such as alkali metal carbonates, for example sodium carbonate, potassium carbonate and sodium bicarbonate; alkali metal alcoholates, for example sodium methylate and potassium methylate; or alkali metal hydroxides, for example sodium hydroxide and potassium hydroxide.

The reaction temperature can be varied within a substantial range in carrying out process variant (a). In general, the reaction is carried out at between 80° and 200° C., preferably between 80° and 150° C.

If appropriate, process variant (a) is carried out under increased pressure. In general, the process is carried out at between 1 and 10 bars.

In carrying out process variant (a), about 1 to 2 moles of the compound of the formula (III) and, if appropriate, about 1 to 2 moles of acid-binding agent are generally employed per mole of butan-2-one derivative. The compounds of the formula (I) are isolated in the customary manner.

Preferred diluents for process variant (b) are water and organic solvents. These include, for example, the solvents which have already been mentioned for process variant (a).

Preferred acid-binding agents for process variant (b) are the compounds which have already been mentioned for process variant (a).

The reaction temperatures can be varied within a substantial range in carrying out process variant (b). In general, the reaction is carried out at between 0° and 120° C., preferably between 20° and 100° C.

In carrying out process variant (b), about 1 to 2 moles of the compound of the formula (V) and, if appropriate, about 1 to 2 moles of acid-binding agent are generally employed per mole of 3,3-dimethyl-4-hydroxy-butan-2-one of the formula (IV). The compounds of the formula (I) are isolated in the customary manner.

Possible oxidizing agents for process variant (c) are any of the inorganic and organic oxidizing agents which can customarily be used. These include, as preferences, organic peracids, for example peracetic acid, p-nitroperbenzoic acid and m-chloroperbenzoic acid; inorganic peracids, for example periodic acid; and also hydrogen peroxide in glacial acetic acid or methanol, potassium permanganate and chromic acid.

The reaction temperatures can be varied within a substantial range in carrying out process variant (c). In general, the reaction is carried out at between about $-50°$ and $+100°$ C., preferably between $-30°$ and $80°$ C.

In carrying out process variant (c), about 1 to 5 moles of oxidizing agent are generally employed per mole of the compound of the formula (Ia). If 1 mole of oxidizing agent, for example m-chloroperbenzoic acid in methylene chloride or hydrogen peroxide in acetic acid, is used at a temperature between $-30°$ and $+30°$ C., the compounds of the formula (I) in which X=SO are preferentially formed. In the case of an excess of oxidizing agent and higher temperatures (10° to 80° C.), the compounds of the formula (I) in which X=SO₂ are preferentially formed. The oxidation products are isolated in the customary manner.

As already mentioned, the 4-substituted 3,3-dimethyl-butan-2-ones of the formula (I) are interesting intermediate products. They can easily be converted into halogeno-ketones of the general formula

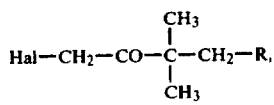

in which
R has the abovementioned meaning and
Hal represents chlorine or bromine, by a process in which chlorine or bromine is added to the compounds of the formula (I) in an inert organic solvent at room temperature, or the compounds of the formula (I) are reacted with, for example, customary chlorinating agents, for example sulphuryl chloride, at from 20° to 60° C.

The halogeno-ketones of the formula (VI) can also be reacted with phenols (in this context, see, for example, the statements in DE-OS (German Published Specification) No. 2,632,603 [Le A 273]), in which case the ether-ketones of the general formula

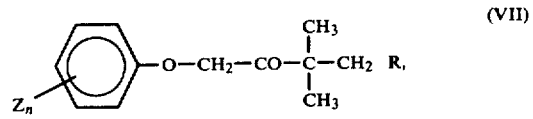

in which
R has the abovementioned meaning,
Z represents halogen, alkyl, alkoxy, nitro, cyano, alkoxycarbonyl or optionally substituted phenyl and
n represents 0, 1, 2 or 3, each Z being selected independently when n is 2 or 3, are obtained. The ether-ketones of the formula (VII) can be converted, by further halogenation, preferably with sulphuryl chloride or with bromine, into the halogenoetherketones of the general formula

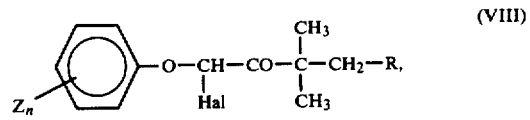

in which Hal, R, Z and n have the abovementioned meaning, which can be smoothly reacted with azoles to give the compounds of the general formula

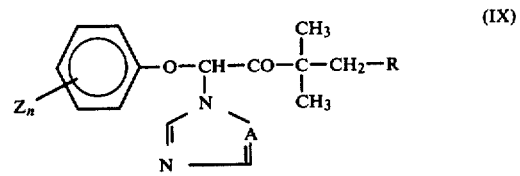

in which
A represents a nitrogen atom or the CH group and
R, Z and n have the abovementioned meaning.

The compounds of the formula (IX) have powerful fungicidal properties and can therefore be used as plant protection agents.

The following comparison test shows, for example, the superior action of 1,4-bis-(4-chlorophenoxy)-3,3-dimethyl-1-(imidazol-1-yl)-butan-2-one in comparison with the compound 1-(4-chlorophenoxy)-4-dichloroacetoxy-3,3-dimethyl-1-(imidazol-1-yl)-butan-2-one, which is known from pending application Ser. No. 819,534, filed July 27, 1977, and is a closely related compound from a chemical point of view:

EXAMPLE 1

Erysiphe test (cucumbers)/protective
Solvent: 4.7 parts by weight of acetone
Emulsifier: 0.3 part by weight of alkylaryl polyglycol ether
Water: 95.0 parts by weight.

The amount of the active compound required for the desired concentration of active compound in the spray liquid was mixed with the stated amount of solvent and the concentrate was diluted with the stated amount of water which contained the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoreacearum*. The plants were subsequently placed in a greenhouse at 23° to 24° C. and at a relative atmospheric humidity of about 75%.

After 12 days, the infection of the cucumber plants was determined. The assessment data were converted to percent infection. 0% denoted no infection and 100% denoted that the plants were totally infected.

The active compounds, active compound concentrations and results can be seen from the following table:

TABLE 1

| Erysiphe test (cucumbers)/protective | |
|---|---|
| Active compound | Infection in % at an active compound concentration of 0.0005% |
| 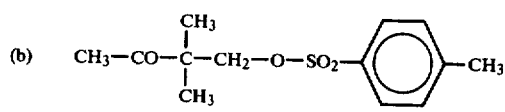 (known) | 100 |
| 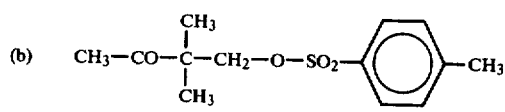 | 12 |

PREPARATIVE EXAMPLES

EXAMPLE 2

(a)   $CH_3-CO-\underset{\underset{CH_3}{|}}{\overset{\overset{CH_3}{|}}{C}}-CH_2OH$ 66 g (2.2 moles) of paraformaldehyde and 1 g of potassium hydroxide in 10 ml of methanol were added dropwise to 172 g (2 moles) of methyl isopropyl ketone in 1,000 ml of methanol. The mixture was heated under reflux for 15 hours and the methanol was then distilled off over a column at an internal temperature of 82° C. The residue was distilled under a waterpump vacuum. 152.7 g (68% of theory) of 2,2-dimethyl-1-hydroxy-butan-3-one of boiling point 80°-82° C./12 mm Hg were obtained.

(b)   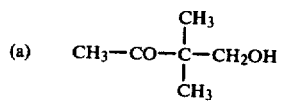

47.6 g (0.25 mole) of 4-toluenesulphonyl chloride were dissolved in 100 ml of chloroform, 35 g (0.3 mole) of 2,2-dimethyl-1-hydroxybutan-3-one were added, and 40 ml (0.5 mole) of pyridine were added dropwise at 0° to 5° C. The reaction mixture was subsequently stirred at room temperature for 15 hours and poured onto 200 g of ice and 70 ml of concentrated hydrochloric acid and the organic phase was separated off, rinsed three times with 200 ml of water each time, dried over sodium sulphate and concentrated. The residue was taken up in 100 ml of petroleum ether, whereupon the end product crystallized out. 48 g (71% of theory) of 2,2-dimethyl-1-tosyloxy-butan-3-one were obtained as colorless crystals of melting point 49°-52° C.

(c)   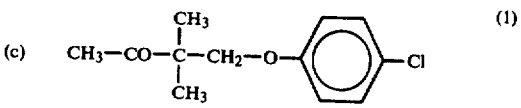   (1)

Process variant (a)

29.7 g (0.55 mole) of sodium methylate were dissolved in 500 ml of methanol, and 70.4 g (0.55 mol) of 4-chlorophenol were added, while stirring. After stirring the mixture for 10 minutes, the solvent was distilled off under reduced pressure and the residue was taken up in 100 ml of glycol. This solution was added to a solution of 135 g (0.5 mole) of 2,2-dimethyl-1-tosyloxy-butan-3-one in 200 ml of glycol. The reaction mixture was stirred at 100° to 120° C. for 48 hours, cooled and stirred into 2,000 ml of water. The mixture was extracted twice with 250 ml of diethyl ether each time and the combined organic phases were washed three times with 100 ml of water each time, once with 100 ml of 10% strength sodium hydroxide solution and once more with 100 ml of water, dried over sodium sulphate and distilled. 62.9 g (55.7% of theory) of 1-(4-chlorophenoxy)-2,2-dimethyl-butan-3-one of boiling point 135°-140° C./0.4 mm Hg were obtained.

EXAMPLE 3

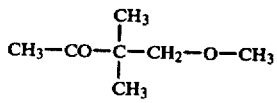   (2)

Process variant (b)

80 g (2 moles) of sodium hydroxide, dissolved in 100 ml of water, were added dropwise to 174 g (1.5 moles) of 2,2-dimethyl-1-hydroxy-butan-3-one (for the preparation, see Example 2a) and 150 ml (2 moles) of dimethyl sulphate at 40° C. (exothermic, slight cooling). After the addition, the mixture was subsequently stirred at 40° C. for 15 hours and the 2,2-dimethyl-1-methoxy-butan-3-one formed was distilled by means of steam. The aqueous phase was saturated with sodium chloride and the oily constituent was separated off and rectified under reduced pressure. 123.8 g (63% of theory) of 2,2-dimethyl-1-methoxy-butan-3-one of boiling point 48°-62° C./5-8 mm Hg were obtained.

EXAMPLE 4

(a)   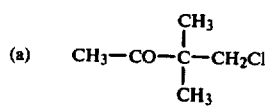

11.6 g (0.1 mole) of 2,2-dimethyl-1-hydroxy-butan-3-one (for the preparation, see Example 2a) were added dropwise to 20.5 g (0.1 mole) of N,N-diethyl-1,2,2-trichlorovinylamine at 50° to 60° C. (cooling with ice). After stirring the mixture at 60° C. for 2 hours, it was distilled under a waterpump vacuum. 8.1 g (60% of theory) of 1-chloro-2,2-dimethyl-butan-3-one of melting point 60°-62° C./12 mm Hg were obtained.

1-Chloro-2,2-dimethyl-butan-3-one was obtained in a yield of 90% when equimolar amounts of 2,2-dimethyl-1-hydroxy-butan-3-one and triphenylphosphine were heated in ten times the amounts of carbon tetrachloride under reflux for 12 hours, the solvent was distilled off, the residue was taken up in ether, the ether mixture was filtered and the filtrate was distilled.

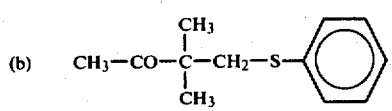

(b)     (3)

Process variant (a)

134.5 g (1 mole) of 4-chloropinacolin were stirred with 165 g (1.5 moles) of thiophenol and 210 g (1.52 moles) of potassium carbonate in 500 ml of dimethylformamide at 150° C. and under a pressure of 2 to 4 bars for 15 hours. The mixture was allowed to cool to room temperature and was stirred with 10 liters of water and extracted with ether. The ether phase was dried over sodium sulphate and concentrated and the residue was distilled in vacuo. 162 g (78% of theory) of 2,2-dimethyl-1-phenylmercapto-butan-3-one of boiling point 112° C./0.5 mm Hg were obtained.

EXAMPLE 5

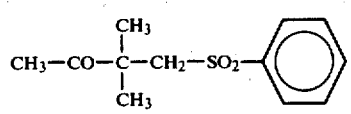

(4)

Process variant (c)

40.6 g (0.2 mole) of 2,2-dimethyl-1-phenylmercapto-butan-3-one (Example 4) were dissolved in 300 ml of glacial acetic acid, and 30.4 g (0.89 mole) of hydrogen peroxide were added. The reaction mixture was stirred at 50° C. for 8 hours. It was then poured into 250 ml of water and extracted with ether. The ether phase was washed with sodium bicarbonate solution, and with water, until neutral, and dried over sodium sulphate and concentrated. 40.4 g (84.2% of theory) of 2,2-dimethyl-1-phenylsulphonyl-butan-3-one of melting point 56°-58° C. were obtained.

The following compounds of the general formula

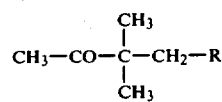

(I)

can be obtained in a manner corresponding to one of Examples 2 to 5 and corresponding to process variant (a), (b) or (c) according to the invention:

| Compound No. | R | Refractive Index or Boiling point (°C.)/mm Hg |
|---|---|---|
| 5 | —O—C$_2$H$_5$ | 54-58/10 |
| 6 | —O—C$_6$H$_3$Cl$_2$ (2,4-Cl) | Oil |
| 7 | —O—C$_6$H$_3$Cl$_2$ (2,6-Cl) | Oil |
| 8 | —O—C$_6$H$_4$—OCH$_3$ | 90-95/0,15 |
| 9 | —O—C$_6$H$_5$ | 83-87/0,15 |
| 10 | —S—CH$_3$ | 80/0,1 |
| 11 | —CN | 85-90/8 |
| 12 | —SCN | 83-87/1 |
| 13 | —S—C$_6$H$_4$—Cl | 146/0,15 |
| 14 | —O—CH$_2$—C$_6$H$_3$Cl$_2$ | 115-23/0,03 |
| 15 | —O—C$_6$H$_4$—Br | 96-110/0,4 |
| 16 | —S—C$_6$Cl$_5$ | melting point 84° C. |
| 17 | —O—CH$_2$—C$_6$H$_4$—Cl | 123/0,01 |
| 18 | —O—C$_6$H$_3$(Cl)(CH$_3$) | $n_D^{20} = 1,5104$ |
| 19 | —O—C$_6$H$_3$(Cl)(CH$_3$) | $n_D^{20} = 1,5108$ |
| 20 | —O—C$_6$H$_3$(CH$_3$)(Cl) | $n_D^{20} = 1,5103$ |
| 21 | —O—C$_6$H$_3$(CH$_3$)(Cl) | $n_D^{20} = 1,5150$ |
| 22 | —O—C$_6$H$_4$—F | $n_D^{20} = 1,4814$ |

-continued

| Compound No. | R | Refractive Index or Boiling point (°C.)/mm Hg |
|---|---|---|
| 23 | 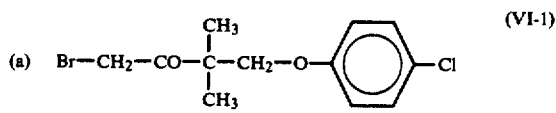 | $n_D^{20} = 1.5301$ |
| 24 | 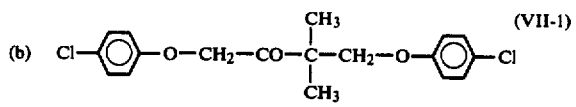 | Fp. = 85–87° C. |

Conversion of the novel intermediates to known fungicides is illustrated in the following example:

EXAMPLE 6

(a) 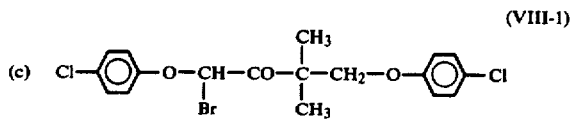 (VI-1)

36 g (0.159 mole) of 1-(4-chlorophenoxy)-2,2-dimethyl-butan-3-one (Example 2) were dissolved in 300 ml of chloroform, and 25.5 g (0.159 mole) of bromine were added dropwise at 20° C. in a manner such that continuous decolorization occurred. After the addition, the mixture was stirred at room temperature for 30 minutes and was then concentrated by distilling off the solvent in vacuo. 48.5 g (quantitative conversion) of crude 1-bromo-4-(4-chlorophenoxy)-3,3-dimethyl-butan-2-one were obtained as an oil.

(b) Cl—⟨O⟩—O—CH₂—CO—C(CH₃)₂—CH₂—O—⟨O⟩—Cl (VII-1)

20.6 g (0.16 mole) of 4-chlorophenol and 28 g (0.2 mole) of potassium carbonate were dissolved in 250 ml of acetone. 48.5 g of 1-bromo-4-(4-chlorophenoxy)-3,3-dimethyl-butan-2-one in 50 ml of acetone were slowly added dropwise, under reflux. After the addition, the mixture was stirred under reflux for 15 hours and filtered and the filtrate was concentrated. The residue was taken up in 500 ml of methylene chloride and the mixture was extracted by shaking with 200 ml of water, 200 ml of saturated sodium bicarbonate solution and again with 200 ml of water.

The organic phase was dried over sodium sulphate and concentrated and the residue was taken up in 150 ml of diisopropyl ether. After concentrating the mixture, 36.6 g (65% of theory) of 1,4-bis-(4-chlorophenoxy)-3,3-dimethyl-butan-2-one were obtained as colorless crystals of melting point 76°–77° C.

(c) Cl—⟨O⟩—O—CH(Br)—CO—C(CH₃)₂—CH₂—O—⟨O⟩—Cl (VIII-1)

36.6 g (0.1 mole) of 1,4-bis-(4-chlorophenoxy)-3,3-dimethyl-butan-2-one were dissolved in 250 ml of chloroform, and 16.6 g (0.1 mole) of bromine were added dropwise at 20° C. in a manner such that continuous decolorization occurred. After the addition, the mixture was subsequently stirred at room temperature for 30 minutes and was then concentrated by distilling off the solvent in vacuo. 43.2 g (quantitative conversion) of 1,4-bis-(4-chlorophenoxy)-1-bromo-3,3-dimethyl-butan-2-one were obtained as an oil, which was further reacted directly.

(d) 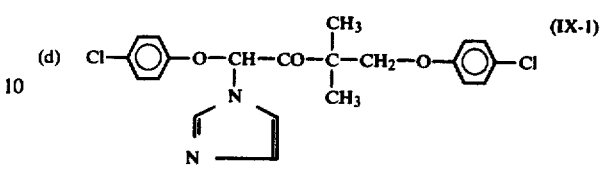 (IX-1)

21.6 g (0.05 mole) of crude 1,4-bis-(4-chlorophenoxy)-1-bromo-3,3-dimethyl-butan-2-one were stirred under reflux with 14 g (0.2 mole) of imidazole in 100 ml of acetonitrile for 17 hours. The mixture was then concentrated by distilling off the solvent under reduced pressure. The residue was taken up in 400 ml of methylene chloride and the mixture was extracted by shaking three times with 800 ml of water each time, dried over sodium sulphate and concentrated. The residue was taken up in 100 ml of acetone, and 9 g (0.05 mole) of 1,5-naphthalenedisulphonic acid tetrahydrate in 50 ml of acetone were added dropwise. The precipitate formed was filtered off and suspended in 200 ml of methylene chloride. 400 ml of saturated sodium bicarbonate solution ere added, the mixture was stirred for 30 minutes and the organic phase was separated off. After distilling off the solvent, 14.1 g (67% of theory) of 1,4-bis-(4-chlorophenoxy)-3,3-dimethyl-1-(imidazol-1-yl)-butan-2-one were obtained as an oil.

It will be appreciated that the instant specification and examples are set forth by way of illustration and not limitation, and that various modifications and changes may be made without departing from the spirit and scope of the present invention.

We claim:
1. A 4-substituted 3,3-dimethyl-butan-2-one of the formula

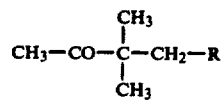

in which
R represents cyano or the grouping —X—R¹, wherein
R¹ represents n-alkyl with 1 to 4 carbon atoms, isopropyl, isobutyl, sec.-butyl, alkenyl with 3 to 4 carbon atoms, alkynyl with 3 to 4 carbon atoms, optionally substituted aryl or substituted aralkyl, or represents cyano provided that X represents —O— or —S—, and
X represents —O—, —S—, —SO—, or —SO₂—.
2. A compound according to claim 1, in which
R represents the grouping —X—R¹ or cyano, and R¹ represents n-alkyl with 1 to 4 carbon atoms, isopropyl, isobutyl or sec.-butyl; alkenyl or alkynyl with in either case 3 to 4 carbon atoms; optionally substituted aryl with 6 to 10 carbon atoms or substituted aralkyl with 6 to 10 carbon atoms in the aryl part and 1 to 2 carbon atoms in the alkyl part, the or each substituent on the aryl in either case being selected from halogen, cyano, nitro, alkoxy-carbonyl with 1 to 4 carbon atoms in the alkyl part, alkyl and alkoxy with in either case 1 to 4 carbon atoms, dialkylamino with 1 to 2 carbon atoms in each alkyl part and phenyl which is itself optionally substituted by halogen; or may represent cyano, provided that X represents oxygen or sulphur.

3. A compound according to claim 1, in which R represents cyano or —X—R$^1$ and R$^1$ represents methyl, ethyl, n-propyl, isopropyl, n-butyl, isobutyl, sec.-butyl, allyl, propargyl or optionally substituted phenyl or substituted benzyl, the or each substituent being selected from fluorine, chlorine, bromine, cyano, nitro, methoxycarbonyl, methyl, ethyl, isopropyl, tert.-butyl, methoxy, dimethylamino and phenyl which is optionally substituted by fluorine and/or chlorine; or R$^1$ represents cyano, provided that X represents oxygen or sulphur.

4. A compound according to claim 1, wherein such compound is 1-(4-chlorophenoxy)-2,2-dimethyl-butan-3-one of the formula

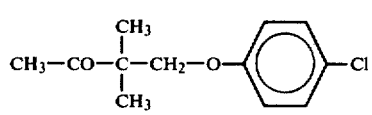

5. A compound according to claim 1, wherein such compound is 1-methoxy-2,2-dimethyl-butan-3-one of the formula

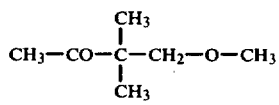

6. A compound according to claim 1, wherein such compound is 1-phenylmercapto-2,2-dimethyl-butan-3-one of the formula

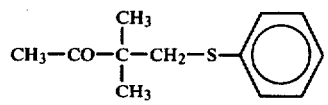

7. A compound according to claim 1, wherein such compound is 1-phenylsulphonyl-2,2-dimethyl-butan-3-one of the formula

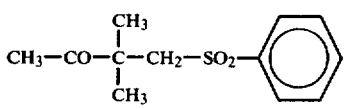

* * * * *